(12) United States Patent
De Strooper et al.

(10) Patent No.: US 8,580,493 B2
(45) Date of Patent: Nov. 12, 2013

(54) SCREENING FOR COMPOUNDS THAT MODULATE GPR3-MEDIATED BETA-ARRESTIN SIGNALING AND AMYLOID BETA PEPTIDE GENERATION

(75) Inventors: Bart De Strooper, Leuven (BE); Amantha Thathiah, Leuven (BE)

(73) Assignees: VIB VZW, Gent (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 0 days.

(21) Appl. No.: 13/376,578

(22) PCT Filed: Jun. 4, 2010

(86) PCT No.: PCT/EP2010/057808
§ 371 (c)(1),
(2), (4) Date: Jan. 17, 2012

(87) PCT Pub. No.: WO2010/142603
PCT Pub. Date: Dec. 16, 2010

(65) Prior Publication Data
US 2012/0136045 A1    May 31, 2012

Related U.S. Application Data

(60) Provisional application No. 61/268,054, filed on Jun. 8, 2009.

(51) Int. Cl.
*C12Q 1/68*    (2006.01)
*C07K 5/00*    (2006.01)
*G01N 33/48*    (2006.01)

(52) U.S. Cl.
USPC ................................. 435/6; 530/300; 436/94

(58) Field of Classification Search
None
See application file for complete search history.

(56) References Cited

U.S. PATENT DOCUMENTS

| | | |
|---|---|---|
| 5,693,761 A | 12/1997 | Queen et al. |
| 5,766,886 A | 6/1998 | Studnicka et al. |
| 5,821,123 A | 10/1998 | Studnicka |
| 5,859,205 A | 1/1999 | Adair et al. |
| 5,869,619 A | 2/1999 | Studnicka |
| 6,054,297 A | 4/2000 | Carter |
| 6,180,370 B1 | 1/2001 | Queen et al. |
| 2003/0143732 A1 | 7/2003 | Fosnaugh et al. |
| 2005/0266502 A1 | 12/2005 | Merchiers et al. |

FOREIGN PATENT DOCUMENTS

| | | |
|---|---|---|
| EP | 626390 A1 | 11/2001 |
| WO | 2008020435 A2 | 2/2008 |
| WO | 20100142603 A1 | 12/2010 |

OTHER PUBLICATIONS

Yin H. et al.; Lipid G Protein-coupled Receptor Ligan Identification Using beta-Arrestin PathHunter (TM) Assay; J. Biol. Chem, vol. 284, No. 18, May 2009; pp. 12328-12338.
Ahn S. et al.; Desensitization, internalization, and signaling functions of beta-arrestins demonstrated by RNA interference; Proc. Nat. Acad. Sci. USA; vol. 100, No. 4; Feb. 18, 2003; pp. 1740-1744.
Thathiah A. et al.; The orphan G protein-coupled receptor 3 modulates amyloid-beta peptide generation in neurons; Science; vol. 323, No. 5916, Feb. 13, 2009; pp. 946-951.
PCT International Search Report PCT/EP2010/057808 dated Jul. 28, 2010.

*Primary Examiner* — Amy Bowman
(74) *Attorney, Agent, or Firm* — TraskBritt

(57) ABSTRACT

The invention relates to the field of disorders of the peripheral or central nervous system, in particular, Alzheimer's disease, and the prevention and/or treatment thereof. In particular, the invention relates to the screening of compounds that modulate GPR3 activity and/or beta-arrestin signaling in a mammalian cell and, in particular, compounds that reduce the formation of amyloid beta peptides. The invention also relates to inhibiting agents targeting beta-arrestin signaling and pharmaceutical compositions thereof, and their use in therapeutic applications of those disorders.

5 Claims, 6 Drawing Sheets

SEQ ID NO: 4

```
   1 cgcgggggtt tctcggggtc cacgcacgcc ctgcgccgcc aggacccgag cggagcctcc
  61 ccgcggcccg gccgcgcctg gtcctgagcg gtaccatgat gtggggtgca ggcagccctc
 121 tggcctggct ctcagctggc tcaggcaacg tgaatgtaag cagcgtgggc ccagcagagg
 181 ggcccacagg tccagccgca ccactgccct cgcctaaggc ctgggatgtg gtgctctgca
 241 tctcaggcac cctggtgtcc tgcgagaatg cgctagtggt ggccatcatc gtgggcactc
 301 ctgccttccg tgccccatg ttcctgctgg tgggcagcct ggccgtggca gacctgctgg
 361 caggcctggg cctggtcctg cactttgctg ctgtcttctg catcggctca gcggagatga
 421 gcctggtgct ggttggcgtg ctggcaatgg cctttaccgc cagcatcggc agtctactgg
 481 ccatcactgt cgaccgctac ctttctctgt acaatgccct cacctactat tcagagacaa
 541 cagtgacacg gacctatgtg atgctggcct tagtgtgggg aggtgccctg ggcctgggc
 601 tgctgcctgt gctggcctgg aactgcctgg atggcctgac cacatgtggc gtggtttatc
 661 cactctccaa gaaccatctg gtagttctgg ccattgcctt cttcatggtg tttggcatca
 721 tgctgcagct ctacgcccaa atctgccgca tcgtctgccg ccatgcccag cagattgccc
 781 ttcagcggca cctgctgcct gcctcccact atgtggccac ccgcaagggc attgccacac
 841 tggccgtggt gcttggagcc tttgccgcct gctggttgcc cttcactgtc tactgcctgc
 901 tgggtgatgc ccactctcca cctctctaca cctatcttac cttgctccct gccacctaca
 961 actccatgat caaccctatc atctacgcct ccgcaacca ggatgtgcag aaagtgctgt
1021 gggctgtctg ctgctgctgt cctcttcca agatccccctt ccgatcccgc tcccccagtg
1081 atgtctagct gagtcttcat gacccttcaa ccctgattac tacagaattc cagaatgtta
1141 ggctctccag ggcttctttc caaacccca gctccacacc cccagaccc agctggttct
1201 ggagttctag gacattgggt gtttcaaggt tctgttcaga tccctatggg ggcccagctg
1261 gctccacggt tccagaatgt tcaggtggtc agtgttctac tcagaaatgt ctcacagccc
1321 agctgggttg caattccaga atgctggag ttttacagtg ccattccaag tcccagatgt
1381 ccctcttccc ccaaacttga ccttgaccat gtcactttac gtttgaattt ctgagctaaa
1441 gagtcagaga gattagtcac atagttgcct aaataggaga gagaaagatt atatatgcac
1501 atatacaaag acagtgtcta tttatgattg atttatttat ttataaattt acttatgggt
1561 ggtaaggggc aaaaaagagg cccacacctt gatatccagg ccataccagg gtatcccttg
1621 tccttcacc cccattctg acctcagttc ctggagggg gaaagggtga aagagaaacc
1681 acgtattttg ttattatttt ggattatttt ttatcgaaga gatcatagaa accagagcct
1741 tctccccagg cctgccctcc tcgggttgg aaggggaaca caccagcctc tggttttta
1801 tttttttaag aagccatcac ctgagcaacc aaaaattcct ctgcgctggg gtccgactgc
1861 cctctggtgg ccatttgggg aaaactgcag cccggccagg cagctgggac cagaatgcaa
1921 ccccagctcc actccagcct ggcgtccagg ccacagcca tggcctgggg gccaagcctc
1981 accctgcggt gccctaaagg agggggca cgagccaaca ccccacccct ctgccaaccg
2041 gggtatggcc cccagtgcat tccctgttcc cgtctccaac ccaactcaat aaaaaatgat
2101 tttgtcataa aaaaaaaaa aaaaaaaaa aaaaaaaaaa aaaaa
```

FIG. 2A

SEQ ID NO: 5

MMWGAGSPLAWLSAGSGNVNVSSVGPAEGPTGPAAPLPSPKAWDVVLCISGTLVSCENALVVAIIVGTPAFRAPMFLL
VGSLAVADLLAGLGLVLHFAAVFCIGSAEMSLVLVGVLAMAFTASIGSLLAITVDRYLSLYNALTYYSETTVTRTYVM
LALVWGGALGLGLLPVLAWNCLDGLTTCGVVYPLSKNHLVVLAIAFFMVFGIMLQLYAQICRIVCRHAQQIALQRHLL
PASHYVATRKGIATLAVVLGAFAACWLPFTVYCLLGDAHSPPLYTYLTLLPATYNSMINPIIYAFRNQDVQKVLWAVC
CCCSSSKIPFRSRSPSDV

FIG. 2B

SEQ ID NO: 6

```
   1 accccgcgcg gttccacgcc cctggccgcg gcccgggcgc tgcgctgctc gacgcggcgg
  61 gcggcggcg ggcaccgggg gcggggcgg cggcggcggc cgggagagcg gaggaggcgg
 121 agcagggagc cgggagcggg ctggcccgcg ctcctcctgc tggctgggga ttttccagcc
 181 tgggcgctga cgccgcggac ctccctgcga ccgtcgcgga ccatgggcga caaagggacc
 241 cgagtgttca agaaggccag tccaaatgga aagctcaccg tctacctggg aaagcgggac
 301 tttgtggacc acatcgacct cgtggaccct gtggatggtg tggtcctggt ggatcctgag
 361 tatctcaaag agcggagagt ctatgtgacg ctgacctgcg ccttccgcta tggccgggag
 421 gacctggatg tcctgggcct gaccttccgc aaggacctgt tgtggccaa cgtacagtcg
 481 ttcccacccg cccccgagga caagaagccc ctgacgcggc tgcaggaacg cctcatcaag
 541 aagctgggcg agcacgctta ccctttcacc tttgagatcc ctccaaacct tccatgttct
 601 gtgacactgc agccggggcc cgaagacacg gggaaggctt gcggtgtgga ctatgaagtc
 661 aaagccttct gcgcggagaa tttggaggag aagatccaca agcggaattc tgtgcgtctg
 721 gtcatccgga aggttcagta tgcccagag aggcctggcc ccagcccac agccgagacc
 781 accaggcagt tcctcatgtc ggacaagccc ttgcacctag aagcctctct ggataaggag
 841 atctattacc atggagaacc catcagcgtc aacgtccacg tcaccaacaa caccaacaag
 901 acggtgaaga gatcaagat ctcagtgcgc cagtatgcag acatctgcct tttcaacaca
 961 gctcagtaca agtgccctgt tgccatggaa gaggctgatg acactgtggc acccagctcg
1021 acgttctgca aggtctacac actgacccc ttcctagcca ataaccgaga gaagcggcgc
1081 ctcgccttgg acgggaagct caagcacgaa gacacgaact tggcctctag cacctgttg
1141 agggaaggtg ccaaccgtga gatcctgggg atcattgttt cctacaaagt gaaagtgaag
1201 ctggtggtgt ctcggggcgg cgacgtggcc gtggaactgc ccttcaccct aatgcacccc
1261 aagcccaaag gggaacccc gcatccagaga accgagacgcc agtagatacc
1321 aatctcatag aacttgacac aaatgatgac gacattgtat ttgaggactt tgctcgccag
1381 agactgaaag gcatgaagga tgacaaggag gaagaggagg atggtaccgg ctctccacag
1441 ctcaacaaca gatagacgg ccggccctgc ctccacgtgg ctccggctcc actctcgtgc
1501 actcggatgc ttactcgtct cttcctgtt ctggttctct ttcccctttg ttcttccagt
1561 ttctaccagg gggccccgtg ggcttccaga tcacggtgat gaacctctgg cctcaggatt
1621 ggccccacat caccacgcca acaggaccac agcgcactgg ctccacccca tctctgccat
1681 ctccactccc ctcctttca tgctgtctcc cagaaaagct gccagggctc tggccttgga
1741 attggacttg agatgggcag cagacagggg aggatgggga atgtgggaca cggtgtggtg
1801 ggcatgaggg cttggagggg tggggatgag ggctcaagac acgagagaag atgtccacgg
1861 tcccaggtgg ttaacaaagt tctggcagct aaaagatgac cgcgttgaag gccacctcct
1921 tctggctggg aggggcagaa ctgtggacag attctcaatg ccttttgaa gttctgaccc
1981 accaaagacc ttctgccttc accctcctcc ccacctgatg tccctctgtg tctgatagtg
2041 atgttggtga aagttcgtag accccaggag tagagaaaag caactggact gactttctta
2101 ccagcagtta cctagactga ggcaagctgt gtggactcac ccaagtatat ttcagtactg
2161 tcaggctgtg acatcttagc
```

FIG. 3A

SEQ ID NO: 7

MGDKGTRVFKKASPNGKLTVYLGKRDFVDHIDLVDPVDGVVLVDPEYLKERRVYVTLTCAFRYGREDLDVLGLTFRKD
LFVANVQSFPPAPEDKKPLTRLQERLIKKLGEHAYPFTFEIPPNLPCSVTLQPGPEDTGKACGVDYEVKAFCAENLEE
KIHKRNSVRLVIRKVQYAPERPGPQPTAETTRQFLMSDKPLHLEASLDKEIYYHGEPISVNVHVTNNTNKTVKKIKIS
VRQYADICLFNTAQYKCPVAMEEADDTVAPSSTFCKVYTLTPFLANNREKRGLALDGKLKHEDTNLASSTLLREGANR
EILGIIVSYKVKVKLVVSRGGDVAVELPFTLMHPKPKEEPPHREVPENETPVDTNLIELDTNDDIVFEDFARQRLKG
MKDDKEEEEDGTGSPQLNNR

FIG. 3B

SEQ ID NO: 8

```
   1 ccccgcgtgt ctgctaggag agggcgggca gcgccgcggc gcgcgcgatc cggctgacgc
  61 atctggcccc ggttccccaa gaccagagcg gggccgggag ggaggggaa gaggcgagag
 121 cgcggagggc gcgcgtgcgc attggcgcgg ggaggagcag ggatcttggc agcgggcgag
 181 gaggctgcga gcgagccgcg aaccgagcgg gcggcgggcg cgcgcaccat ggggagaaa
 241 cccgggacca gggtcttcaa gaagtcgagc cctaactgca agctcaccgt gtacttgggc
 301 aagcgggact tcgtagatca cctggacaaa gtggaccctg tagatggcgt ggtgcttgtg
 361 gaccctgact acctgaagga ccgcaaagtg tttgtgaccc tcacctgcgc cttccgctat
 421 ggccgtgaag acctggatgt gctgggcttg tccttccgca agaccttt catcgccacc
 481 taccaggcct tcccccccggt gcccaaccca cccggcccc caccgcct gcaggaccgg
 541 ctgctgagga agctgggcca gcatgcccac cccttcttct tcaccatacc ccagaatctt
 601 ccatgctccg tcacactgca gccaggccca gaggatacag gaaaggcctg cggcgtagac
 661 tttgagattc gagccttctg tgctaaatca ctagaagaga aagccacaa aggaactct
 721 gtgcggctgg tgatccgaaa ggtgcagttc gccccggaga aacccggccc cagccttca
 781 gccgaaacca cacgccactt cctcatgtct gaccggtccc tgcacctcga ggcttccctg
 841 gacaaggagc tgtactacca tggggagccc ctcaatgtaa atgtccacgt caccaacaac
 901 tccaccaaga ccgtcaagaa gatcaaagtc tctgtgagac agtacgccga catctgcctc
 961 ttcagcaccg cccagtacaa gtgtcctgtg gctcaactcg aacaagatga ccaggtatct
1021 ccagctcca cattctgtaa ggtgtacacc ataaccccac tgctcagcga caaccgggag
1081 aagcgggtc tcgccctgga tgggaaactc aagcacgagg acaccaacct ggcttccagc
1141 accatcgtga aggagggtgc caacaaggag gtgctggaa tcctggtgtc ctacagggtc
1201 aaggtgaagc tggtggtgtc tcgaggcggg gatgtctctg tggagctgcc ttttgttctt
1261 atgcacccca agccccacga ccacatcccc ctccccagac ccagtcagc cgctccggag
1321 acagatgtcc ctgtggacac caacctcatt gaatttgata ccaactatgc cacagatgat
1381 gacattgtgt ttgaggactt tgcccggctt cggctgaagg ggatgaagga tgacgactat
1441 gatgatcaac tctgctagga agcggggtgg gaagaaggga ggggatgggg ttgggacagg
1501 tgagggcagg attaagatcc ccactgtcaa tgggggattg tcccagcccc tcttcccttc
1561 ccctcacctg gaagcttctt caaccaatcc cttcacactc tctcccccat cccccaaga
1621 tacacactgg accctctctt gctgaatgtg ggcattaatt ttttgactgc agctctgctt
1681 ctccagcccc gccgtgggtg gcaagctgtg ttcataccta aattttctgg aaggggacag
1741 tgaaaagagg agtgacagga gggaaggggg gagacaaaac tcctactctc aacctcacac
1801 caacacctcc cattatcact ctctctgccc ccattccttc aagaggagac cctttgggga
1861 caaggccgtt tctttgtttc tgagcataaa gaagaaaata aatcttttac taagcatgaa
1921 aaaaaaaaaa aaaaaa
```

FIG. 4A

SEQ ID NO: 9

MGEKPGTRVFKKSSPNCKLTVYLGKRDFVDHLDKVDPVDGVVLVDPDYLKDRKVFVTLTCAFRYGREDLDVLGLSFRK
DLFIATYQAFPPVPNPPRPPTRLQDRLLRKLGQHAHPFFFTIPQNLPCSVTLQPGPEDTGKACGVDFEIRAFCAKSLE
EKSHKRNSVRLVIRKVQFAPEKPGPQPSAETTRHFLMSDRSLHLEASLDKELYYHGEPLNVNVHVTNNSTKTVKKIKV
SVRQYADICLFSTAQYKCPVAQLEQDDQVSPSSTFCKVYTITPLLSDNREKRGLALDGKLKHEDTNLASSTIVKEGAN
KEVLGILVSYRVKVKLVVSRGGDVSVELPFVLMHPKPHDHIPLPRPQSAAPETDVPVDTNLIEFDTNYATDDDIVFED
FARLRLKGMKDDDYDDQLC

FIG. 4B

SCREENING FOR COMPOUNDS THAT MODULATE GPR3-MEDIATED BETA-ARRESTIN SIGNALING AND AMYLOID BETA PEPTIDE GENERATION

CROSS-REFERENCE TO RELATED APPLICATIONS

This is a national phase entry under 35 U.S.C. §371 of International Patent Application PCT/EP2010/057808, filed Jun. 4, 2010, published in English as International Patent Publication WO 2010/142603 A1 on Dec. 16, 2010, which claims the benefit under Article 8 of the Patent Cooperation Treaty and 35 U.S.C. §119(e) to U.S. Provisional Patent Application Ser. No. 61/268,054, filed Jun. 8, 2009.

TECHNICAL FIELD

The invention relates to the field of disorders of the peripheral or central nervous system, in particular, Alzheimer's disease, and the prevention and/or treatment thereof. In particular, the invention relates to the screening of compounds that modulate GPR3 activity and/or beta-arrestin signaling in a mammalian cell, more particularly, compounds that reduce the formation of amyloid beta peptides. The invention also relates to inhibiting agents targeting beta-arrestin signaling and pharmaceutical compositions thereof, and their use in therapeutic applications of those disorders.

BACKGROUND

Alzheimer's disease (AD) is the most common neurodegenerative disorder afflicting the elderly. AD is clinically characterized by progressive neuronal loss and inflammation, memory impairment, cognitive deficits, and behavioral changes. Neuropathologically, the AD brain is characterized by two proteinaceous aggregates, amyloid plaques, mainly composed of the amyloid β-protein (Aβ), and neurofibrillary tangles (NFT), comprised of hyperphosphorylated aggregates of the tau protein (Selkoe 2001). Two major hypotheses have driven pharmaceutical research in the search for a medication for AD: the amyloid hypothesis (Hardy and Selkoe 2002) and the cholinergic hypothesis (Bartus et al. 1982). Although significant progress has been made toward understanding the pathophysiology of AD, significant questions remain unanswered, e.g., the potential link between amyloid pathology and the cholinergic deficit observed in AD patients and the relationship between Aβ generation, neuronal cell death, and NFTs.

Aβ is derived from proteolysis of the β-amyloid precursor protein (APP), a type I integral membrane protein, following sequential cleavage by the β- and γ-secretases. The γ-secretase is a tetrameric complex that cleaves APP within its transmembrane domain, thereby liberating the intact Aβ peptide, which ranges in length from 39-43 residues (De Strooper et al. 2003). The majority of Aβ produced is 40 amino acids in length ($A\beta_{40}$), whereas a small proportion (~10%) is the 42-residue variant ($A\beta_{42}$). $A\beta_{42}$ is more hydrophobic, aggregates much faster than $A\beta_{40}$, is more toxic than $A\beta_{40}$, and is the major Aβ species found in cerebral plaques (Selkoe 2001; Iwatsubo 1994).

Despite intensive research during the last 100 years, prognosis of AD patients now is still quite the same as that of patients a century ago, since there is still no real cure available. There are two types of drugs approved by the U.S. Food and Drug Administration and used in clinic today to treat AD: Acetylcholinesterase (AchE) inhibitors and Memantine. There is ample evidence in the art that the amyloid beta peptide, the main component of the amyloid plaques that are specific to the AD etiology, has a key role in the development of AD disease (Hardy et al. 2002; Golde et al. 2006). Therefore, one of the most common strategies to lower Aβ is to diminish its production by γ- and β-secretase inhibition. One strategy was the development of gamma-secretase inhibitors; however, such inhibitors often result in serious side effects since gamma-secretase is involved in the proteolytic processing of at least 30 proteins (De Strooper et al. 2003). Yet another attractive strategy is the development of β-secretase (BACE1) inhibitors, as BACE1 knock-out mice are viable and have no obvious pathological phenotype (e.g., Roberds et al. 2001; Ohno et al. 2004; Ohno et al. 2006). Yet, there still is a continuous need for alternative approaches to lower Aβ in view of treating patients with neurodegenerative disorders, such as Alzheimer's disease.

DISCLOSURE

The invention relates to modulating the function of seven-transmembrane receptors (7TMRs), also known as G-protein-coupled receptors (GPCRs), via the selective recruitment of beta-arrestin, thus influencing amyloid-beta peptide formation in mammalian cells.

GPCRs are the largest, most versatile, and most ubiquitous of the several families of plasma membrane receptors. These receptors regulate virtually all known physiological processes in mammals. Moreover, they are the most common targets of currently used therapeutic drugs. GPCR function is mediated and modulated through two ubiquitous and generic mechanisms: G-protein activity and β-arrestin function. Therapeutics targeting GPCRs include agonists, partial agonists and antagonists, based on a two-state model of receptor activation and the concept that activation is dependent on association with heterotrimeric G-proteins. Different subclasses of Gα proteins, such as Gαs, Gαi, Gαq and Gα12, signal through distinct pathways involving second messenger molecules, such as cAMP, inositol triphosphate (IP3), diacylglycerol, intracellular $Ca^{2+}$ and RhoA GTPases. β-arrestin proteins, as the name suggests, were originally discovered to "arrest" G-protein-mediated cell signaling events, a process also known as desensitization. However, in addition to their classical role, β-arrestin proteins also act as adapters that couple GPCRs to a clathrin-coated pit endocytic mechanism, and as scaffolds that link GPCRs to a second wave of cell signaling via mitogen-activated protein kinase (MAPK), and other signaling pathways as well, independently from G-protein signaling.

G-protein-coupled receptor 3 (GPR3), a constitutively active orphan G-protein-coupled receptor (GPCR), is a known modulator of Aβ production (Thathiah et al. 2009). The level of expression of GPR3 regulates localization of the γ-secretase complex, thereby affecting the amyloidogenic processing of APP, which suggests that GPR3 is an interesting AD therapeutic target. Although GPR3 is an orphan GPCR, a putative ligand has been identified (Nyabi et al. 2003), and GPR3 constitutively elevates cAMP levels via adenylate cyclase activation (Herreman et al. 2003; Oddo et al. 2006), implying that it intrinsically activates the G-protein G. On the other hand, G-protein coupling does not appear to be a prerequisite for GPR3-mediated regulation of Aβ release (Thathiah et al. 2009).

The invention is based on our surprising finding that β-arrestin activity is necessary for the formation of amyloid beta peptides in mammalian cells.

Accordingly, in a first aspect, the invention relates to a method for identifying a compound that modulates GPR3 activity and/or beta-arrestin signaling in a mammalian cell comprising contacting a test compound with a GPR3 polypeptide and determining the effect of the test compound on beta-arrestin signaling in a G-protein-independent fashion. In particular, this screening method aims at identifying compounds that reduce amyloid beta peptide formation in a mammalian cell and as such can be used for the prevention and/or treatment of a disorder of the peripheral or central nervous system, in particular, Alzheimer's disease. Advantageously, the compound is an allosteric modulator of the GPR3 target.

Another aspect of the invention relates to an inhibitory agent that it is reducing amyloid beta peptide formation, wherein the agent is a small interfering RNA (siRNA), and wherein the agent comprises a nucleic acid sequence engineered from a β-arrestin 1 or β-arrestin 2 encoding polynucleotide. In particular, the agent may comprise a nucleic acid molecule chosen from SEQ ID NOS:1-3. Further, the agent can be used as a medicament, more specifically for use in the prevention and/or treatment of a disorder of the peripheral or central nervous system, in particular, Alzheimer's disease.

In a further aspect, the invention relates to a pharmaceutical composition comprising a therapeutically effective amount of the above-described inhibitory agent and at least one of a pharmaceutically acceptable carrier, adjuvant or diluent. In still another aspect, the inhibitory agent or pharmaceutical composition can be used for the manufacture of a medicament to prevent and/or treat a disorder of the peripheral or central nervous system, in particular, Alzheimer's disease.

BRIEF DESCRIPTION OF THE DRAWINGS

FIGS. 2A and 2B: Nucleotide (FIG. 2A) and amino acid (FIG. 2B) sequence of human GPR3, respectively defined by SEQ ID NOS:4 and 5.

FIGS. 3A and 3B: Nucleotide (FIG. 3A) and amino acid (FIG. 3B) sequence of human β-arrestin 1, respectively defined by SEQ ID NOS:6 and 7.

FIGS. 4A and 4B: Nucleotide (FIG. 4A) and amino acid (FIG. 4B) sequence of human β-arrestin 2, respectively defined by SEQ ID NOS:8 and 9.

DETAILED DESCRIPTION OF THE INVENTION

Definitions

Figure 1A:
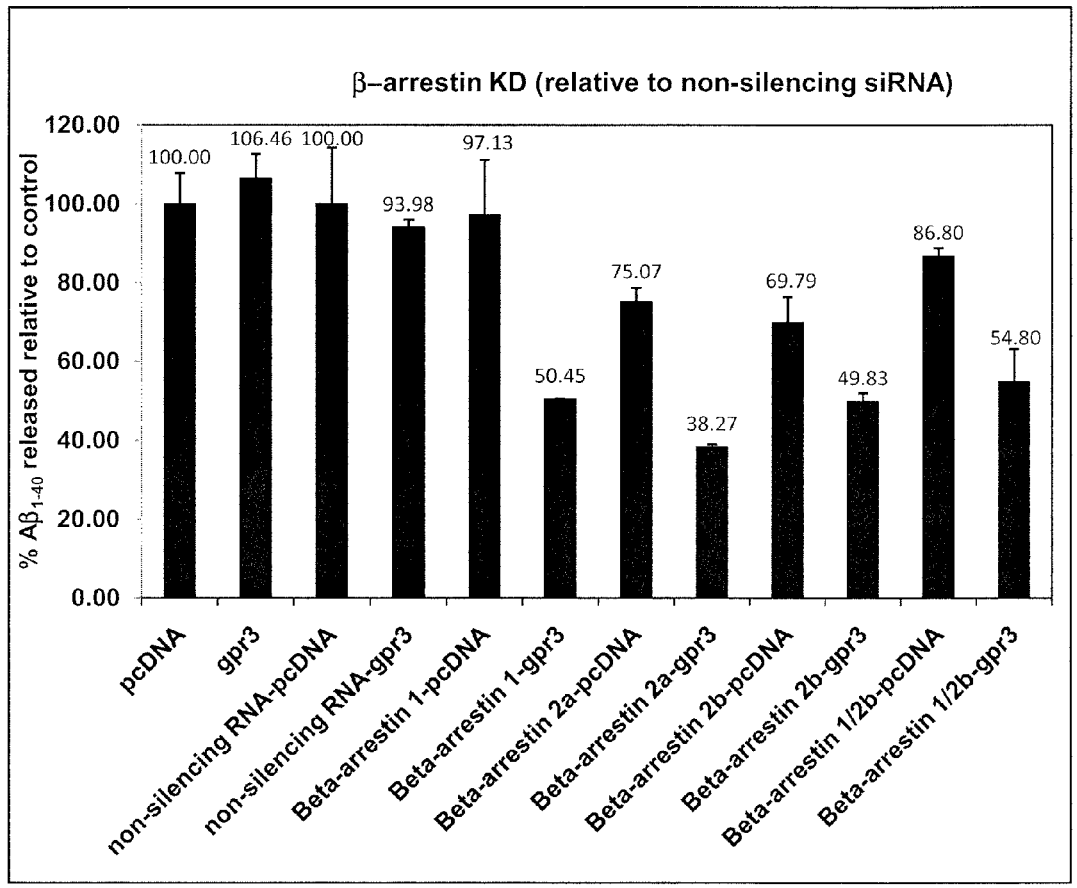
FIGS. 1A and 1B: Effect of siRNA-mediated β-arrestin depletion on $A\beta_{1-40}$ (FIG. 1A) and $A\beta_{1-42}$ (FIG. 1B) generation in HEK293 $APP_{695}$ cells. Cells were transfected with pcDNA or GPR3, and siRNA targeting β-arrestin 1, 2, both, or a non-silencing (control) RNA duplex prior to measurement of $A\beta_{1-40}$ (FIG. 1A) and $A\beta_{1-42}$ (FIG. 1B) secretion in cell culture supernatants by ELISA. The results are expressed as the mean percentage ±SD of three independent experiments performed in duplicate relative to non-silencing siRNA (control).

The term "agonist" refers to a ligand that, by binding a receptor, increases the receptor's activity.

The term "antagonist" refers to a ligand that binds a receptor without stimulating any activity. An "antagonist" is also known as a "blocker" because of its ability to prevent binding of other ligands and, therefore, block agonist-induced activity.

The term "inverse agonist" refers to an antagonist that, in addition to blocking agonist effects, reduces receptors' basal, constitutive activity.

The term "partial agonist" refers to an agonist that results in a sub-maximal response, even when receptors are fully occupied. Partial agonists can also function as "blockers" by preventing the binding of more robust agonists.

The term "ligand bias" is the ability of a ligand to selectively stimulate a subset of a receptor's activities. Such ligands are known as "biased ligands," "biased agonists" or "functionally selective agonists."

The terms "amyloid beta peptide" or "amyloid beta protein" or "Aβ peptide" or "Aβ" are interchangeably used further herein. Amyloid beta peptides are processed from the amyloid beta precursor protein (APP) and include the amyloid beta peptides 1-42, 1-40, 11-42, 11-40, which can be found in plaques and are often seen in cerebral spinal fluid.

The terms "beta-arrestin" or "β-arrestin" refer to the non-visual arrestins, β-arrestin 1 (sometimes referred to as Arrestin 2) and β-arrestin 2 (sometimes referred to as Arrestin 3), and play a central role in GPCR desensitization and sequestration, but also in linking GPCRs to cellular signaling systems, such as MAP kinase cascades amongst others, the latter in the invention also referred to as "beta-arrestin signaling."

The term "compound" is used herein in the context of a "test compound" or a "drug candidate compound" described in connection with the methods of the invention. As such, these compounds comprise organic or inorganic compounds, derived synthetically or from natural resources. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies or antibody conjugates.

The terms "modulating," "modulation," "modulated," "inhibiting," "inhibition," "inhibited" mean an up-regulation or down-regulation of the expression, or an increase or decrease in activity of a protein. Modulation of a protein includes the up-regulation, down-regulation, increase or decrease in activity of a protein or compound that regulates a protein. Modulation also includes the regulation of a gene, the mRNA, or any other step in the synthesis of the protein of interest.

The terms "allosteric modulator" or "allosteric inhibitor" in the context of the invention refer to noncompetitive modulators or inhibitors, which exert their effect by binding to a site other than the active site of the receptor, and modulate the activity of the receptor or render the receptor ineffective in terms of signal transduction. A "positive allosteric modulator (PAM)" increases signal transduction, whereas a "negative allosteric modulator (NAM)" reduces signal transduction.

The terms "protein," "polypeptide," and "peptide" are interchangeably used further herein.

The terms "polynucleotide," "polynucleic acid," and "nucleic acid" are interchangeably used further herein.

The term "antibody" refers to a protein or polypeptide having affinity for an antigen or for an antigenic determinant. Such an antibody is commonly composed of four chains, two heavy and two light chains, and is thus tetrameric. An exception thereto are camel antibodies that are composed of heavy chain dimers and are devoid of light chains, but nevertheless have an extensive antigen-binding repertoire. An antibody usually has both variable and constant regions whereby the variable regions are mostly responsible for determining the specificity of the antibody and will comprise complementarity-determining regions (CDRs).

The term "specificity" refers to the ability of an immunoglobulin, such as an antibody, to bind preferentially to one antigenic target versus a different antigenic target and does not necessarily imply high affinity.

The term "affinity" refers to the degree to which an immunoglobulin, such as an antibody, binds to an antigen so as to shift the equilibrium of antigen and antibody toward the presence of a complex formed by their binding. Thus, where an antigen and antibody are combined in relatively equal concentration, an antibody of high affinity will bind to the available antigen so as to shift the equilibrium toward high concentration of the resulting complex.

The terms "complementarity-determining region" or "CDR" refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, H3) for the respective light (L) and heavy (H) chains. The accepted CDR regions have been described by Kabat et al. (1991).

The terms "therapeutically effective amount," "therapeutically effective dose" and "effective amount" mean the amount needed to achieve the desired result or results (e.g., inhibiting β-arrestin signaling; treating or preventing Alzheimer's disease).

"Pharmaceutically acceptable" means a material that is not biologically or otherwise undesirable, i.e., the material may be administered to an individual along with the compound without causing any undesirable biological effects or interacting in a deleterious manner with any of the other components of the pharmaceutical composition in which it is contained.

The term "subject" includes humans and other mammals.

The Concept of the Invention

A first aspect of the invention relates to a method for identifying a compound that modulates GPR3 activity and/or beta-arrestin signaling in a mammalian cell comprising:
  i. contacting a test compound with a GPR3 polypeptide;
  ii. determining the effect of the test compound on beta-arrestin signaling in a G-protein-independent fashion.

A particular embodiment of the above method relates to identifying a compound that reduces amyloid beta peptide formation in a mammalian cell comprising:
  i. contacting a test compound with a GPR3 polypeptide;
  ii. determining the effect of the test compound on beta-arrestin signaling in a G-protein-independent fashion;
  iii. measuring the amount of amyloid beta peptide produced.

In a preferred embodiment of the above methods, the compound is an allosteric modulator of the GPR3 polypeptide target, in particular, a positive allosteric modulator (PAM) or a negative allosteric modulator (NAM).

In another preferred embodiment, the compound is a therapeutic candidate for the treatment of a disorder of the peripheral or central nervous system, in particular, Alzheimer's disease.

The polynucleotide sequence of the human G-protein-coupled receptor 3 (GPR3) is accessible in public databases by the reference number NM_005281.2 and is given by SEQ ID NO:4 (see also FIG. 2A). The amino acid sequence of GPR3 is given by SEQ ID NO:5 (see also FIG. 2B). The GPR3 polypeptide as referred to in the invention also includes active fragments of the full-length GPR3 polypeptide. "Active," with respect to the GPR3 polypeptide, refers to those forms, fragments or domains of a GPR3 polypeptide that retain the biological and/or antigenic activity of a GPR3 polypeptide. GPR3 is described as a receptor for sphingosine 1-phosphate (Uhlenbrock et al. 2002), suggesting a role in sphingosine 1-phosphate-mediated intracellular signaling. GPR3 is predominantly expressed in the central nervous system (Blacker et al. 2003; Tanaka et al. 2007).

Beta-arrestins (non-visual arrestins) are ubiquitously expressed proteins that were first described for their role in desensitizing G-protein-coupled receptors (GPCRs). There are two β-arrestins, namely β-arrestin 1 and β-arrestin 2. They were first identified for their ability to "arrest" agonist-stimulated β2 adrenergic receptor signaling (Lohse et al. 1990) in a manner similar to regulation of rhodopsin. The canonical model of GPCR regulation by β-arrestins also involves GPCR kinases (GRKs) that phosphorylate receptors and thereby serve to facilitate receptor-β-arrestin interactions. Upon complexing with receptors, β-arrestins can serve as inhibitors of signal transduction by preventing further receptor coupling to G-protein signaling cascades (Lefkowitz 1998). Besides their role in desensitization, beta-arrestin 1 and 2 promote the formation of signaling complexes allowing GPCRs to signal independently from G-proteins. The polynucleotide sequences of human β-arrestin 1 and 2 are accessible in public databases, respectively, by the reference numbers NM_020251.2 and NM_004313.3, and is also given by SEQ ID NOS:6 and 8, respectively (see also FIGS. 3A/4A). The amino acid sequences of β-arrestin 1 and 2 are given by SEQ ID NOS:7 and 9, respectively (see also FIGS. 3B/4B).

In the invention, the above-described screening methods are to be understood as methods to identify compounds that can bind to GPR3, whether or not hereby modulating GPR3 activity, and that via binding to GPR3, can selectively or preferentially modulate beta-arrestin signaling over G-protein signaling. More specifically, such "biased" β-arrestin-mediated signaling occurs in the absence of G-protein-mediated signaling. Even more specifically, the compounds identified within the context of the invention are meant to be biased agonists/antagonists, selectively or preferentially modulating β-arrestin signaling and not heterotrimeric G-protein signaling. It should be clear to the skilled person that the selectivity of the biased agonists/antagonists is not absolute. On the other hand, it should also be clear that the biased agonists/antagonists are different from conventional agonists/antagonists, that are defined here as modulating signaling through both heterotrimeric G-proteins and β-arrestins. To clarify this further, a conventional antagonist binding a GPCR prevents agonist-stimulated signaling through heterotrimeric G-proteins and β-arrestins. In contrast, a biased antagonist/agonist blocks agonist-stimulated heterotrimeric G-protein signaling while promoting β-arrestin signaling.

The invention is based on the aforesaid discovery that β-arrestin activity is necessary for the processing of amyloid beta precursor protein in mammalian cells and may, therefore, be useful in reducing or lowering the levels of amyloid beta peptides in a subject in need thereof. The present methods comprise contacting a test compound or a drug candidate compound with a GPR3 polypeptide, or an active fragment of the polypeptide, and determining or measuring the effect of the test compound on beta-arrestin signaling in a G-protein-independent fashion. Preferably, the amount of amyloid beta peptide produced is also measured in the present methods to be sure that the candidate drug compound would be useful for reducing amyloid beta peptide levels when administered to a subject.

As said, the candidate drug compound may be an allosteric modulator of GPR3. Allosteric modulators are an emerging class of orally available small molecule therapeutic agents that may offer patients better results relative to classical drugs. This potential stems from their ability to offer greater selectivity and better modulatory control of disease-mediating receptors. Allosteric modulators do not compete with endogenous ligands and, therefore, can exert their influence even if an endogenous ligand is bound to another site on the same target at the same time. By contrast, classical orthosteric drugs compete with endogenous ligands for the same site on a given target. This means that lower doses of allosteric modulators can have greater potency than orthosteric molecules with similar affinity. In other words, allosteric modulators could have fewer side effects compared to orthosteric molecules addressing the same target. Allosteric modulators can also be devoid of activity in the absence of endogenous ligands. As a result, allosteric modulators may offer a less disruptive way to influence the functioning of biological systems. They do not perturb signaling on their own. Thus, they could preserve more of the natural biology in comparison to orthosteric approaches. Specifically, this could lead to greater safety and fewer side effects.

Assay methods that can be used in the context of the invention are described hereafter, without the purpose of being limiting. It should be clear to the skilled artisan that the present screening methods might be based on a combination or a series of measurements, particularly when establishing the link with amyloid beta peptide generation. Also, it should be clear that there is no specific order in performing these measurements while practicing the invention.

The simplest assays of β-arrestin activity are measures of β-arrestin translocation to receptors in the presence or absence of the candidate ligand. β-arrestin activity is usually measured via fluorescently tagged β-arrestins monitored with either microscopic imaging of β-arrestin redistribution to activated receptors or with fluorescence resonance energy transfer (FRET) (Barak et al. 1997) or bioluminescence resonance energy transfer (BRET) (Bertrand et al. 2002; Vilardaga et al. 2003) assays that detect the interaction of β-arrestins and receptors. Such assays offer the advantage of being intrinsically specific for β-arrestin and the GPCR of interest. However, these assays suffer from limited sensitivity. Unlike measurements of G-protein or β-arrestin signals, which are enzymatically amplified, β-arrestin recruitment assays operate stoichiometrically as a function of the proportion of receptors bound to β-arrestin. Thus, it can be difficult to detect weak partial agonists for β-arrestin recruitment.

A modified β-galactosidase complementation assay, referred to as PathHunter™ technology, is another preferred assay method (Olson and Eglen 2007). The principle of the assay is the detection of an interaction between GPR3 and β-arrestin following receptor activation. The assay is unique because it provides a direct measure of β-arrestin binding, whereas imaging assays detect the movement of β-arrestin. In this system, the β-galactosidase enzyme is split into two inactive fragments. The assay makes use of a low affinity peptide derived from the amino-terminus of *Escherichia coli* β-galactosidase, which is tethered to the carboxy-terminus of GPR3 (ProLink™ tag), and a w-deletion mutant of β-galactosidase, which is fused to β-arrestin (enzyme acceptor or EA). The use of the low-affinity ProLink™ peptide ensures that the enzyme fragment complementation (EFC) reaction is driven by the receptor-stimulated, reversible interaction of GPR3 with β-arrestin and not by β-galactosidase complementation in the absence of receptor stimulation. Thus, complementation between β-arrestin and GPR3 results in the formation of a functional enzyme that is capable of hydrolyzing a substrate and generating a chemiluminescent signal. Given the finding that β-arrestin modulates Aβ release, the PathHunter™ β-arrestin assay would facilitate the identification of potential allosteric modulators of Aβ generation. Regarding the latter, the AllostericScreener™ (Millipore) is another example of an assay method that can be used alone or in combination with any of the described assay methods.

Following the identification of putative β-arrestin-activated compounds, a secondary validation assay is necessary to verify that β-arrestin activation correlates with a modulation of Aβ levels by measuring Aβ generation. Determining the level of amyloid beta peptides produced can be done by using specific ELISAs using antibodies specifically recognizing the different amyloid beta peptides species (see, e.g., Example 1).

Additional validation assays are also necessary to determine whether the test compounds are selectively directed to beta-arrestin signaling in a G-protein-independent fashion or to ascertain that G-protein activation is not inversely affecting β-arrestin recruitment. Such assay methods include, but are not limited to, measuring the biological activity of the GPCR by determining the level of cyclic AMP accumulation or of another second messenger such as $Ca^{2+}$, cyclic GMP, inositol triphosphate (IP3) and/or diacylglycerol (DAG) in the presence or absence of the candidate ligand. As a non-limiting example of a cAMP assay, the ALPHASCREEN® cAMP assay kit (Perkin Elmer) can be used. Detection of cAMP with ALPHASCREEN® is based on the competition between cAMP produced by cells and a biotinylated cAMP probe that is recognized by the streptavidin-Donor and anti-cAMP-conjugated acceptor beads. The beads are brought into proximity and a signal is detected. Increased intracellular concentrations of cAMP following $G_s$-coupled GPCR activation by an agonist results in displacement of the biotinylated cAMP probe and leads to a proportional signal decrease. G-protein activity can also be assayed, for example, by determining phosphatidylinositol turnover, GTP-γ-S loading, adenylate cyclase activity, GTP hydrolysis, etc., in the presence or absence of the candidate ligand (see, for example, Kostenis 2006).

The efficacies for G-protein activity and β-arrestin function for a given test compound or candidate ligand acting on GPR3, or an active fragment thereof, can be determined by assays in eukaryotic cells, advantageously in mammalian cells, such as human cells. Appropriate assays can also be performed in prokaryotic cells, reconstituted membranes, and using purified proteins in vitro.

For high-throughput purposes, compound libraries may be used in conjunction with, e.g., the PathHunter™ β-arrestin assay to identify modulators of β-arrestin activation. Examples include, but are not limited to, allosteric compound libraries, peptide libraries, antibody fragment libraries, synthetic compound libraries, natural compound libraries, etc.

Polypeptide therapeutics and, in particular, antibody-based therapeutics have significant potential as drugs because they have exquisite specificity to their target and a low inherent toxicity. In particular, the features of monoclonal antibodies such as high affinity, high selectivity, and distinct structure and function domains amenable to protein engineering for therapeutic delivery, make them potential drug candidates. Given the growing potential for the utilization of monoclonal antibodies as therapeutics, GPR3-specific monoclonal antibodies can be generated using techniques well-known by the skilled person as these form part of the current state of the art and the effectiveness of these antibodies as modulators of Aβ generation can also be determined in the context of the invention.

Active fragments of the above-described antibodies also form part of the invention. The term "active fragment" refers to a portion of an antibody that, by itself, has high affinity for an antigenic determinant, or epitope, and contains one or more CDRs accounting for such specificity. Non-limiting examples include Fab, F(ab)'2, scFv, heavy-light chain dimers, nanobodies, domain antibodies, and single-chain structures, such as a complete light chain or complete heavy chain.

The antibodies of the invention, or their active fragments, can be labeled by an appropriate label, the label can, for instance, be of the enzymatic, colorimetric, chemiluminescent, fluorescent, or radioactive type.

It is known by the skilled person that an antibody that has been obtained for a therapeutically useful target requires additional modification in order to prepare it for human therapy in order to avoid an unwanted immunological reaction in a human individual upon administration. The modification process is commonly termed "humanization." It is known by the skilled artisan that antibodies raised in species, other than in humans, require humanization to render the antibody therapeutically useful in humans ((1) CDR grafting: Protein Design Labs: U.S. Pat. No. 6,180,370, U.S. Pat. No. 5,693,761; Genentech U.S. Pat. No. 6,054,297; Celltech: EP626390, U.S. Pat. No. 5,859,205; (2) Veneering: Xoma: U.S. Pat. No. 5,869,619, U.S. Pat. No. 5,766,886, U.S. Pat. No. 5,821,123). Humanization of antibodies entails recombinant DNA technology, and is departing from parts of rodent and/or human genomic DNA sequences coding for H and L chains or from cDNA clones coding for H and L chains. Techniques for humanization of non-human antibodies are known to the skilled person as these form part of the current state of the art. Non-human mammalian antibodies or animal antibodies can be humanized (see, for instance, Winter and Harris 1993). The antibodies or monoclonal antibodies according to the invention may be humanized versions of, for instance, rodent antibodies or rodent monoclonal antibodies.

In a second aspect, the invention relates to an inhibitory agent, such as an antisense polynucleotide, a ribozyme, or a small interfering RNA (siRNA), characterized in that it is reducing amyloid beta peptide formation, and wherein the agent comprises a nucleic acid sequence complementary to, or engineered from, a β-arrestin 1 or β-arrestin 2 encoding polynucleotide.

In a preferred embodiment, the inhibitory agents of the invention encompass short interfering RNA (siRNA) molecules that down-regulate expression of a beta-arrestin mRNA by RNA interference. RNA interference refers to the process of sequence-specific post transcriptional gene silencing in animals mediated by short interfering RNAs (siRNA) (Fire et al. 1998). siRNA molecules are short pieces of dsRNA obtained by processing of the dsRNA by Dicer, a ribonuclease III enzyme (Bernstein et al. 2001). Short interfering RNAs derived from Dicer activity are typically about 21-23 nucleotides in length and comprise about 19 base pair duplexes. siRNAs up to 26 nucleotides have proven to be effective at specifically silencing gene expression without causing any interferon response. The siRNA molecules of the invention encompass human beta-arrestin siRNAs, which are useful for research to analyze the function of beta-arrestin, and which may be used for therapy in humans, e.g., in the prevention and/or treatment of a disorder of the peripheral or central nervous system, in particular, Alzheimer's disease. In a specific embodiment, the small interfering RNAs (siRNA) of the present invention comprise a nucleic acid sequence as defined by SEQ ID NOS:1-3 (Table 1).

TABLE 1

Specific siRNAs for β-arrestin 1 and β-arrestin 2.

| Gene | Full sequence siRNA (sense strand) | SEQ ID NO: |
|---|---|---|
| β-arrestin 1 | 5'-AAAGCCUUCUGCGCGGAGAAU-3' | 1 |
| β-arrestin 2a | 5'-AAGGACCGCAAAGUGUUUGUG-3' | 2 |
| β-arrestin 2b | 5'-AACCAACCUCAUUGAAUUUGA-3' | 3 |

Based on the RNA sequence of human beta-arrestin, siRNA molecules with the ability to knock down beta-arrestin activity can be obtained by chemical synthesis or by hairpin siRNA expression vectors (as described by Yu et al. 2002). There are numerous companies that provide the supply of customer-designed siRNAs on a given RNA sequence, e.g., Ambion, Imgenex, Dharmacon.

The beta-arrestin siRNAs of the invention may be chemically modified, e.g., as described in US20030143732, by phosphorothioate internucleotide linkages, 2'-O-methyl ribonucleotides, 2'-deoxy-2'-fluoro ribonucleotides, "universal base" nucleotides, 5-C-methyl nucleotides, and inverted deoxyabasic residue incorporation. The sense strand of beta-arrestin siRNAs may also be conjugated to small molecules or peptides, such as membrane-permeant peptides or polyethylene glycol (PEG). Other siRNA conjugates that form part of the invention include cholesterol and alternative lipid-like molecules, such as fatty acids or bile-salt derivatives.

In a further embodiment, the invention relates to an expression vector comprising any of the above-described polynucleotide sequences encoding at least one β-arrestin siRNA molecule in a manner that allows expression of the nucleic acid molecule, and cells containing such vector. The polynucleic acid sequence is operably linked to regulatory signals (promoters, enhancers, suppressors, etc.) enabling expression of the polynucleic acid sequence and is introduced into a cell utilizing, preferably, recombinant vector constructs. A variety of viral-based systems are available, including adenoviral, retroviral, adeno-associated viral, lentiviral, and herpes simplex viral vector systems. Selection of the appropriate viral vector system, regulatory regions and host cell is common knowledge within the level of ordinary skill in the art.

As gene delivery and gene silencing techniques improve, the selective deletion of β-arrestins in particular tissues or cellular populations may prove useful in order to limit the impact of protein deletion to a particular system under study. The beta-arrestin siRNA molecules of the invention may be delivered by known gene delivery methods, e.g., as described in US 20030143732, including the use of naked siRNA, synthetic nanoparticles composed of cationic lipid formulations, liposome formulations including pH-sensitive liposomes and immunoliposomes, or bioconjugates including siRNAs conjugated to fusogenic peptides. Delivery of siRNA-expressing vectors can be systemic, such as by intravenous or intramuscular administration or by any other means that would allow for introduction into the desired target cell (see US 20030143732).

In still another aspect, the invention relates to a pharmaceutical composition comprising a therapeutically effective amount of any of the above-described inhibitory agents and at least one of a pharmaceutically acceptable carrier, adjuvant or diluents. Any of the above inhibitory agents or pharmaceutical composition can be used for the manufacture of a medicament to prevent and/or treat a disorder of the peripheral or central nervous system, in particular, Alzheimer's disease. One of ordinary skill in the art will recognize that the potency and, therefore, an "effective amount" can vary for the inhibitory agents of the invention. One skilled in the art can readily assess the potency of the inhibitory agent.

A medicament to prevent and/or to treat a disorder of the peripheral or central nervous system, in particular, Alzheimer's disease, relates to a composition comprising inhibitory agents as described above and a pharmaceutically acceptable carrier or excipient (both terms can be used interchangeably) to treat or to prevent diseases as described herein.

The administration of pharmaceutical compositions may be by way of oral, inhaled or parenteral administration. In particular, pharmaceutical compositions can be delivered through intrathecal or intracerebroventricular administration. The active ingredient may be administered alone or preferably formulated as a pharmaceutical composition. An amount effective to treat Alzheimer's disease depends on the usual factors, such as the nature and severity of the disorder being treated and the weight of the mammal. It is greatly preferred that the pharmaceutical composition is administered in the form of a unit-dose composition, such as a unit dose oral, parenteral, or inhaled composition. Such compositions are prepared by admixture and are suitably adapted for oral, inhaled or parenteral administration, and as such, may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like.

Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid and, if desired, conventional flavoring or coloring agents. Oral formulations also include conventional sustained release formulations, such as tablets or granules having an enteric coating.

Preferably, compositions for inhalation are presented for administration to the respiratory tract as a snuff or an aerosol or solution for a nebulizer, or as a microtine powder for insufflation, alone or in combination with an inert carrier such as lactose. In such a case, the particles of active compound suitably have diameters of less than 50 microns, preferably less than 10 microns, for example, between 1 and 5 microns, such as between 2 and 5 microns. For parenteral administration, fluid unit dose forms are prepared containing a compound of the invention and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline, and corticosteroids such as prednisolone, and adrenal stimulants such as ACTH, may be included. As is common practice, the compositions will usually be accompanied by written or printed directions for use in the medical treatment concerned.

A "carrier" or "adjuvant," in particular, a "pharmaceutically acceptable carrier" or "pharmaceutically acceptable adjuvant" is any suitable excipient, diluent, carrier and/or adjuvant that, by themselves, do not induce the production of antibodies harmful to the individual receiving the composition nor do they elicit protection. Preferably, a pharmaceutically acceptable carrier or adjuvant enhances the immune response elicited by an antigen. Suitable carriers or adjuvantia typically comprise one or more of the compounds included in the following non-exhaustive list: large slowly metabolized macromolecules, such as proteins, polysaccharides, polylactic acids, polyglycolic acids, polymeric amino acids, amino acid copolymers, and inactive virus particles.

A "diluent," in particular, a "pharmaceutically acceptable vehicle," includes vehicles such as water, saline, physiological salt solutions, glycerol, ethanol, etc. Auxiliary substances, such as wetting or emulsifying agents, pH buffering substances, preservatives may be included in such vehicles.

It should be clear that the inhibitory agents of the invention for Alzheimer's disease can also be used in combination with any other AD disease therapy known in the art such as gamma-secretase inhibitors, or beta-secretase inhibitors.

EXAMPLES

Example 1

β-Arrestin Activity is Necessary for the Formation of Amyloid Beta Peptides in Mammalian Cells

Chemically synthesized, double-stranded siRNAs targeting β-arrestin 1 or 2 with 19-nucleotide duplex RNA and 2-nucleotide 3'-dTdT overhangs containing fluorescent tags to determine transfection efficiency were purchased from Qiagen. The sequences of the siRNA have been previously described (Ahn et al. 2003; 2004; see also Table 1). As a control, non-silencing siRNA with the sequence 5'-AAUUCUCCGAACGUGUCACGU-3' (SEQ ID NO:10) was used in the experiment. Forty to fifty percent confluent human embryonic kidney (HEK)-293 cells growing in 100-mm dishes and stably expressing wild-type APP (695-amino acid isoform) were transfected with 20 µg of siRNA and 2 µg of a plasmid containing the coding region of human GPR3 using the GeneSilencer Transfection reagent (Genlantis) as previously described by Ahn et al. (2003). Forty-eight hours following transfection, cells were divided into twelve-well plates for β-arrestin immunoblot analysis and further experiments. Twenty-four hours after plating, cells were placed in serum-free medium. Culture supernatant samples were collected the next day for determination of $A\beta_{1-40}$ and $A\beta_{1-42}$ generation. For the measurement of secreted $A\beta_{1-40}$ and $A\beta_{1-42}$, specific ELISA kits (The Genetics Company) were utilized according to the manufacturer's protocol.

Figure 1B:
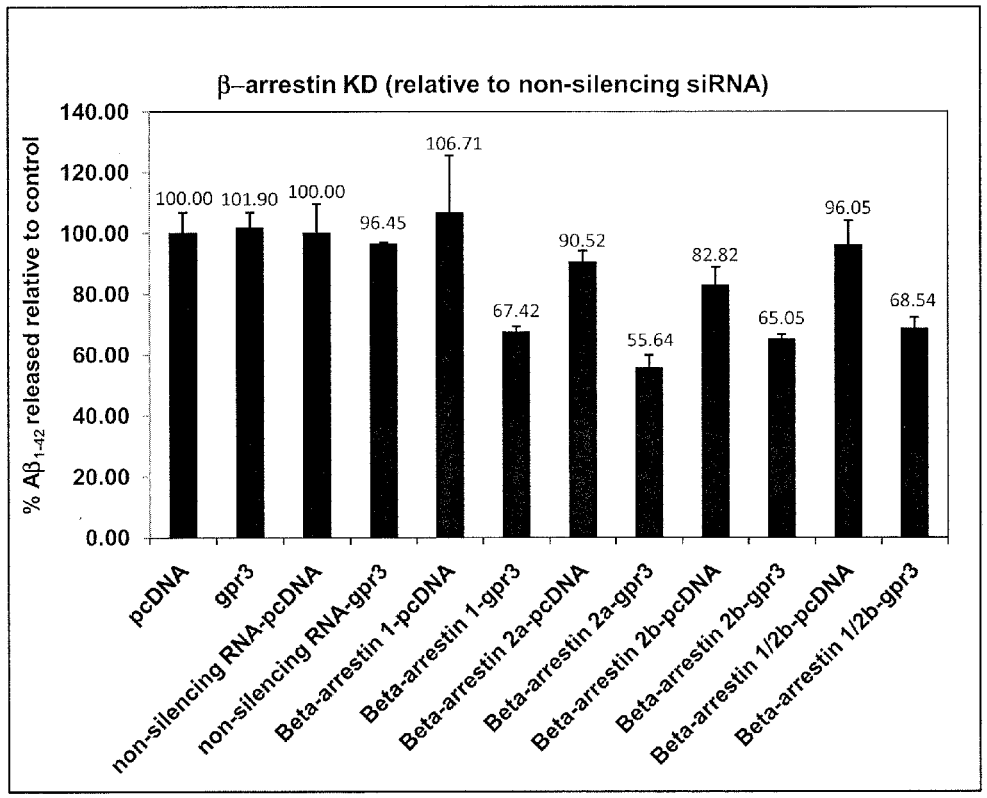

To directly determine the requirement of β-arrestin 1 or 2 for constitutive and GPR3-mediated Aβ generation, Aβ levels were measured in HEK293 $APP_{695}$ cells following transfection with siRNA that specifically targets either β-arrestin 1 or 2 or both. β-arrestin 2 siRNA reduced constitutive $A\beta_{1-40}$ and $A\beta_{1-42}$ generation. Moreover, co-transfection of GPR3 with siRNA directed toward either β-arrestin 1 or 2 or both led to a further reduction in $A\beta_{1-40}$ and $A\beta_{1-42}$ generation (FIG. 1). These studies indicate that β-arrestin 2 participates in constitutive Aβ generation and that both β-arrestin 1 and 2 contribute to Aβ secretion in cells that express GPR3. Thus, signaling cascades initiated by GPR3/β-arrestin-coupling modulate secretion of Aβ, suggesting that GPR3, β-arrestin 1 and 2 are intimately associated mediators of cellular Aβ levels.

Example 2

β-Arrestin Recruitment to GPR3 is Necessary for the Formation of Amyloid Beta Peptides in Mammalian Cells

Figure 5:
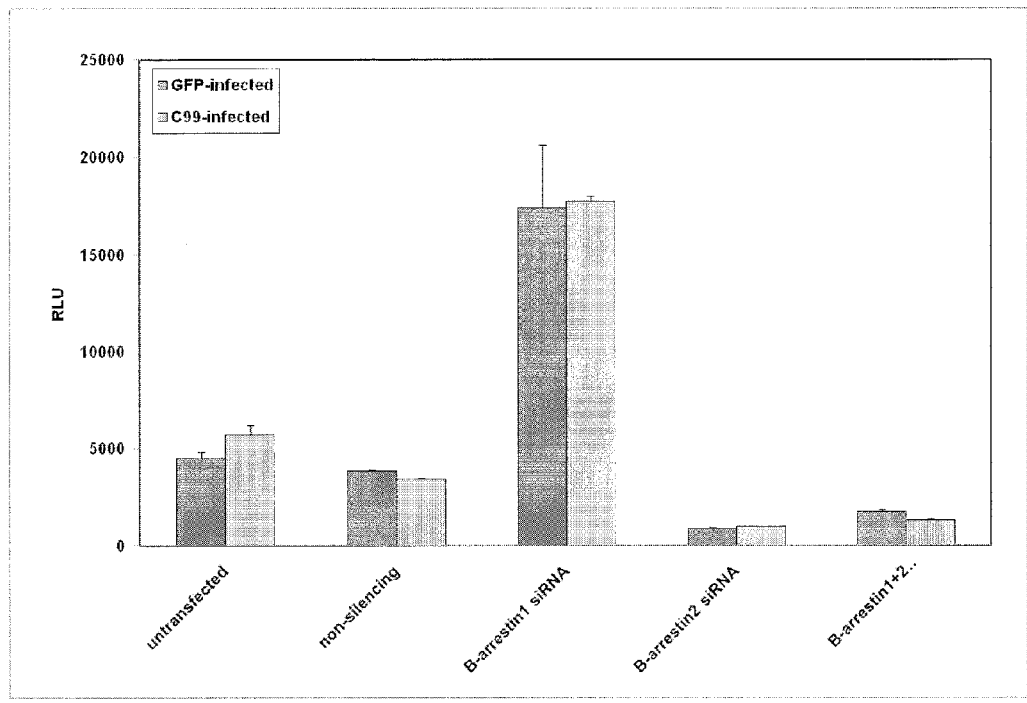
FIG. 5: PathHunter assay to determine β-arrestin activation following β-arrestin 1 and/or 2 knockdown.

Chemically synthesized, double-stranded siRNAs targeting β-arrestin 1 or 2 with 19-nucleotide duplex RNA and 2-nucleotide 3'-dTdT overhangs containing fluorescent tags to determine transfection efficiency were purchased from Qiagen. The sequences of the siRNA have been previously described (Aim et al. 2003; 2004; see also Table 1). As a control, non-silencing siRNA with the sequence 5'-AAUUCUCCGAACGUGUCACGU-3' (SEQ ID NO:10) was used in the experiment. The PathHunter™ Chinese hamster ovary (CHO) GPR3 β-arrestin 2 cell line, which stably expresses GPR3 and β-arrestin 2, was transfected with 20 µg of siRNA using the GeneSilencer Transfection reagent (Genlantis) as previously described by Aim et al. (2003). Forty-eight hours following transfection, cells were divided into six-well and 96-well plates for further experiments. Twenty-four hours after plating, cells were placed in serum-free medium for an additional 24 hours. The PathHunter™ β-arrestin assay was performed on the cells in the 96-well plate to determine the extent of β-arrestin 2 recruitment to GPR3 following a reduction in the expression of β-arrestin 1 or β-arrestin 2. Following β-arrestin 1 knockdown, a clear increase in β-arrestin 2 recruitment to GPR3 is observed by the dramatic increase in chemiluminescent signal, suggesting that β-arrestin 1 is involved in regulating the recruitment of β-arrestin 2 to GPR3. As expected, following a reduction in β-arrestin 2 expression, a significant decrease in chemiluminescence is observed, similar to the effect observed in cells that been targeted with both β-arrestin 1 and 2 siRNA (FIG. 5).

Figure 6:
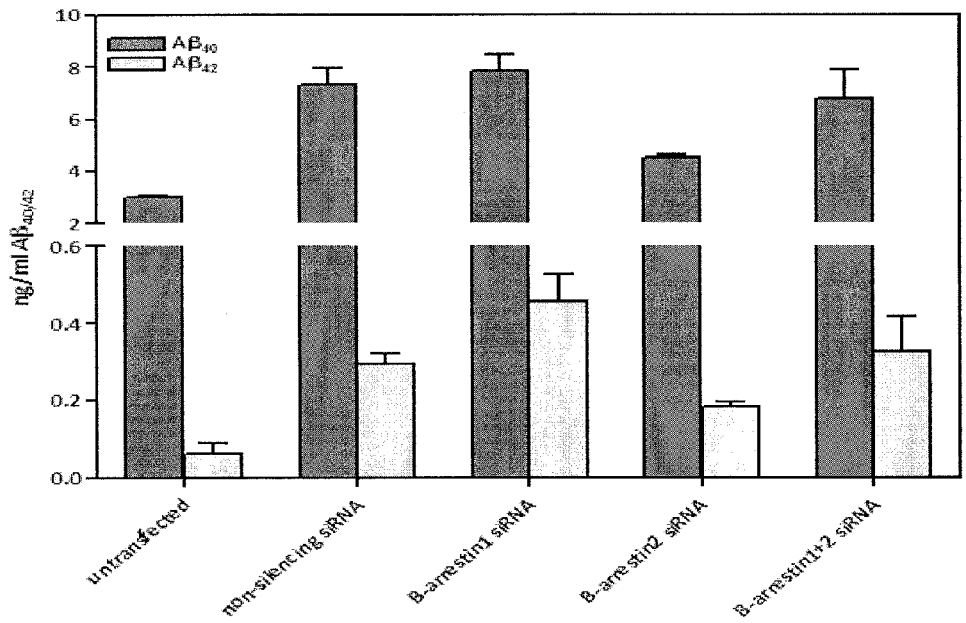
FIG. 6: Knockdown of β-arrestin 2 leads to reduction in $A\beta_{40}$ and $A\beta_{42}$ generation.

Culture supernatant samples were collected from cells seeded in the six-well plates to determine the effect of a reduction in β-arrestin 2 recruitment to GPR3 on $A\beta_{1-40}$ and $A\beta_{1-42}$ generation. For the measurement of secreted $A\beta_{1-40}$ and $A\beta_{1-42}$, specific ELISA kits (The Genetics Company) were utilized according to the manufacturer's protocol. To directly determine the requirement of β-arrestin 1 or 2 for GPR3-mediated Aβ generation, Aβ levels were measured in CHO/β-arrestin 2/GPR3 cells following transfection with siRNA that specifically targets either β-arrestin 1 or 2 or both. β-arrestin 2 siRNA reduced $A\beta_{1-40}$ and $A\beta_{1-42}$ generation, whereas transfection with β-arrestin 1 siRNA did not affect reduced $A\beta_{1-40}$ generation and modestly stimulated $A\beta_{1-42}$ generation in this cellular context. Co-transfection with siRNA directed toward both β-arrestin 1 or 2 also led to a reduction in $A\beta_{1-40}$ and $A\beta_{1-42}$ generation (FIG. 6). These studies indicate that the direct recruitment of β-arrestin 2 to GPR3 is involved in Aβ generation and that both β-arrestin 1 and 2 contribute to Aβ secretion in cells that express GPR3. Thus, signaling cascades initiated by GPR3/β-arrestin coupling modulate secretion of Aβ, suggesting that GPR3, β-arrestin 1 and 2 are intimately associated mediators of cellular Aβ levels.

REFERENCES

Ahn S., S. K. Shenoy, H. Wei, and R. J. Lefkowitz. Differential kinetic and spatial patterns of beta-arrestin and G-protein-mediated ERK activation by the angiotensin II receptor. *J. Biol. Chem.* 279:35518-25 (2004).

Ahn S., C. D. Nelson, T. R. Garrison, W. E. Miller, and R. J. Lefkowitz. Desensitization, internalization, and signaling functions of beta-arrestins demonstrated by RNA interference. *PNAS.* 100:1740-4 (2003).

Barak L. S., S. S. Ferguson, J. Zhang, and M. G. Caron. A beta-arrestin/green fluorescent protein biosensor for detecting G-protein-coupled receptor activation. *J. Biol. Chem.* 272:27497-500 (1997).

Bartus R. T., R. L. Dean 3rd, B. Beer, and A. S. Lippa. The cholinergic hypothesis of geriatric memory dysfunction. *Science* 217:408 (1982).

Bertrand L., S. Parent, M. Caron, M. Legault, E. Joly, S. Angers, M. Bouvier, M. Brown, B. Houle, and L. Ménard. The BRET2/arrestin assay in stable recombinant cells: a platform to screen for compounds that interact with G-protein-coupled receptors (GPCRS). *J. Recept. Signal Transduct. Res.* 22:533-41 (2002).

Blacker D, L. Bertram, A. J. Saunders, T. J. Moscarillo, M. S. Albert, H. Wiener, R. T. Perry, J. S. Collins, L. E. Harrell, R. C. Go, A. Mahoney, T. Beaty, M. D. Fallin, D. Avramopoulos, G. A. Chase, M. F. Folstein, M. G. McInnis, S. S. Bassett, K. J. Doheny, E. W. Pugh, R. E. Tanzi; and NIMH Genetics Initiative Alzheimer's Disease Study Group. Results of a high-resolution genome screen of 437 Alzheimer's disease families. *Hum. Mol. Genet.* 12:23-32 (Jan. 1, 2003).

De Strooper B. Aph-1, Pen-2, and Nicastrin with Presenilin generate an active gamma-Secretase complex. *Neuron* 38:9-12 (2003).

Golde T. E., D. Dickson, and M. Hutton. Filling the gaps in the abeta cascade hypothesis of Alzheimer's disease. *Curr. Alzheimer Res.* 3:421-30 (2006).

Hardy J., and D. J. Selkoe. The amyloid hypothesis of Alzheimer's disease: progress and problems on the road to therapeutics. *Science* 297:353-6 (2002).

Herreman A., G. Van Gassen, M. Bentahir, O, Nyabi, K. Craessaerts, U. Mueller, W. Annaert, and B. De Strooper. gamma-Secretase activity requires the presenilin-dependent trafficking of nicastrin through the Golgi apparatus but not its complex glycosylation. *J. Cell. Sci.* 116:1127-36 (Mar. 15, 2003).

Iwatsubo T., A. Odaka, N. Suzuki, H. Mizusawa, N. Nukina, and Y. Ihara. Visualization of A beta 42(43) and A beta 40 in senile plaques with end-specific A beta monoclonals: evidence that an initially deposited species is A beta 42(43). *Neuron* 13:45-53 (1994).

Kabat E. A., and T. T. Wu. Identical V region amino acid sequences and segments of sequences in antibodies of different specificities. Relative contributions of VH and VL genes, minigenes, and complementarity-determining regions to binding of antibody-combining sites. *The Journal of Immunology*, 147(5): 1709-19 (1991).

Kostenis E. G-proteins in drug screening: from analysis of receptor-G-protein specificity to manipulation of GPCR-mediated signaling pathways. *Curr. Pharm. Res.* 12:1703-1715 (2006).

Lefkowitz R. J. G-protein-coupled receptors. III. New roles for receptor kinases and beta-arrestins in receptor signaling and desensitization. J. Biol. Chem. 273:18677-80 (1998).

Lohse M. J., J. L. Benovic, J. Codina, M. G. Caron, and R. J. Lefkowitz. beta-Arrestin: a protein that regulates beta-adrenergic receptor function. *Science* 248:(4962):1547-50 (1990).

Nyabi O., M. Bentahir, K. Hone, A. Herreman, N. Gottardi-Littell, C. Van Broeckhoven, P. Merchiers, K. Spittaels, W. Annaert, and B. De Strooper. Presenilins mutated at Asp-257 or Asp-385 restore Pen-2 expression and Nicastrin glycosylation but remain catalytically inactive in the absence of wild-type Presenilin. *J. Biol. Chem.* 278:43430-6 (2003).

Oddo S., V. Vasilevko, A. Caccamo, M. Kitazawa, D. H. Cribbs, and F. M. LaFerla. Reduction of soluble Abeta and tau, but not soluble Abeta alone, ameliorates cognitive decline in transgenic mice with plaques and tangles. *J. Biol. Chem.* 281:39413-23 (2006).

Ohno M., E. A. Sametsky, L. H. Younkin, H. Oakley, S. G. Younkin, M. Citron, R. Vassar, and J. F. Disterhoft. BACE1 Deficiency Rescues Memory Deficits and Cholinergic Dysfunction in a Mouse Model of Alzheimer's Disease. *Neuron* 41:27-33 (2004).

Ohno M., L. Chang, W. Tseng, H. Oakley, M. Citron, W. L. Klein, R. Vassar, and J. F. Disterhoft. Temporal memory deficits in Alzheimer's mouse models: rescue by genetic deletion of BACE1. *Eur. J. Neurosci.* 23:251-260 (2006).

Olson K. R., and R. M. Eglen. Beta galactosidase complementation: a cell-based luminescent assay platform for drug discovery. *Assay Drug Dev. Technol.* 5:137-44 (2007).

Roberds S. L., J. Anderson, G. Basi, M. J. Bienkowski, D. G. Branstetter, K. S. Chen, S. B. Freedman, N. L. Frigon, D. Games, and K. Hu, et al, BACE knockout mice are healthy despite lacking the primary β-secretase activity in brain: implications for Alzheimer's disease therapeutics. *Hum. Mol. Genet.* 10:1317-1324 (2001).

Selkoe D. J. Alzheimer's disease: genes, proteins, and therapy. *Physiol. Rev.* 81:741-66 (2001).

Tanaka S., K. Ishii, K. Kasai, S. O. Yoon, and Y. Saeki. Neural expression of G-protein-coupled receptors GPR3, GPR6, and GPR12 up-regulates cyclic AMP levels and promotes neurite outgrowth. *J. Biol. Chem.* 282:10506-15 (2007).

Thathiah A., K. Spittaels, M. Hoffmann, M. Staes, A. Cohen, K. Horre, M. Vanbrabant, F. Coun, V. Baekelandt, A. Delacourte, D. F. Fischer, D. Pollet, B. De Strooper, and P. Merchiers. The orphan G-protein-coupled receptor 3 modulates amyloid-beta peptide generation in neurons. *Science* 323:(5916):946-51 (2009).

Uhlenbrock K., H. Gassenhuber, and E. Kostenis. Sphingosine 1-phosphate is a ligand of the human gpr3, gpr6 and gpr12 family of constitutively active G-protein-coupled receptors. *Cell Signal* 14(11):941-53 (2002).

Vilardaga et al. Measurement of the millisecond activation switch of G-protein-coupled receptors in living cells. *Nat. Biotechnol.* 21:807-12 (2003).

Winter G., and W. J. Harris. Humanized antibodies. *Trends Pharmacol. Sci.* 14(5):139-43 (1993).

---

The invention claimed is:

1. A method for identifying a compound that modulates GPR3 activity and/or beta-arrestin signaling in a mammalian cell, the method comprising:
   i. contacting a test compound with a GPR3 polypeptide in the mammalian cell,
   ii. determining the effect of said test compound on beta-arrestin signaling in a G protein-independent fashion in the mammalian cell, and
   iii. measuring the amount of amyloid beta peptide produced in the mammalian cell so as to identify a compound that reduces amyloid beta peptide formation in the mammalian cell.

2. The method according to claim 1, wherein said amyloid beta peptide is at least one of amyloid beta peptide 1-42, 1-40, 11-42, and 11-40.

3. The method according to claim 1, wherein said compound is an allosteric modulator of a GPR3 target.

4. The method according to claim 1, wherein said compound is a therapeutic candidate for preventing and/or treating a disorder of the peripheral or central nervous system.

5. A method for identifying a compound that modulates GPR3 activity and/or beta-arrestin signaling in a mammalian cell so as to identify a compound that reduces amyloid beta peptide formation in a mammalian cell, the method comprising:
   contacting a test compound with a GPR3 polypeptide in the mammalian cell,
   determining the test compound's effect on beta-arrestin signaling in a G protein-independent fashion in the mammalian cell, and
   measuring amyloid beta peptide production by the mammalian cell, wherein the amyloid beta peptide is at least one of amyloid beta peptides 1-42, 1-40, 11-42, and 11-40.

* * * * *

SEQUENCE LISTING

```
<160> NUMBER OF SEQ ID NOS: 10

<210> SEQ ID NO 1
<211> LENGTH: 21
<212> TYPE: RNA
<213> ORGANISM: Homo sapiens

<400> SEQUENCE: 1
aaagccuucu gcgcggagaa u                                             21

<210> SEQ ID NO 2
<211> LENGTH: 21
<212> TYPE: RNA
<213> ORGANISM: Homo sapiens
```

```
<400> SEQUENCE: 2
aaggaccgca agugutuugu g                                              21

<210> SEQ ID NO 3
<211> LENGTH: 21
<212> TYPE: RNA
<213> ORGANISM: Homo sapiens

<400> SEQUENCE: 3
aaccaaccuc auugaauuug a                                              21

<210> SEQ ID NO 4
<211> LENGTH: 2145
<212> TYPE: DNA
<213> ORGANISM: Homo sapiens

<400> SEQUENCE: 4
cgcgggggtt tctcggggtc cacgcacgcc ctgcgccgcc aggacccgag cggagcctcc      60
ccgcggcccg gccgcgcctg gtcctgagcg gtaccatgat gtggggtgca ggcagccctc     120
tggcctggct ctcagctggc tcaggcaacg tgaatgtaag cagcgtgggc ccagcagagg     180
ggcccacagg tccagccgca ccactgccct cgcctaaggc ctgggatgtg gtgctctgca     240
tctcaggcac cctggtgtcc tgcgagaatg cgctagtggt ggccatcatc gtgggcactc     300
ctgccttccg tgcccccatg ttcctgctgg tgggcagcct ggccgtggca gacctgctgg     360
caggcctggg cctggtcctg cactttgctg ctgtcttctg catcggctca gcggagatga     420
gcctggtgct ggttggcgtg ctggcaatgg cctttaccgc cagcatcggc agtctactgg     480
ccatcactgt cgaccgctac ctttctctgt acaatgccct cacctactat tcagagacaa     540
cagtgacacg gacctatgtg atgctggcct tagtgtgggg aggtgccctg ggcctggggc     600
tgctgcctgt gctggcctgg aactgcctgg atggcctgac acatgtggc gtggtttatc      660 cactctccaa gaaccatctg gtagttctgg ccattgcctt cttcatggtg tttggcatca     720
tgctgcagct ctacgcccaa atctgccgca tcgtctgccg ccatgcccag cagattgccc     780
ttcagcggca cctgctgcct gcctcccact atgtggccac ccgcaagggc attgccacac     840
tggccgtggt gcttggagcc tttgccgcct gctggttgcc cttcactgtc tactgcctgc     900
tgggtgatgc ccactctcca cctctctaca cctatcttac cttgctccct gccacctaca     960
actccatgat caaccctatc atctacgcct tccgcaacca ggatgtgcag aaagtgctgt    1020
gggctgtctg ctgctgctgt tcctcttcca agatccccct ccgatcccgc tcccccagtg    1080
atgtctagct gagtcttcat gacccttcaa ccctgattac tacagaattc cagaatgtta    1140
ggctctccag ggcttctttc caaaccccca gctccacacc ccccgaccc agctggttct     1200 ggagttctag acattgggt gtttcaaggt tctgttcaga tccctatggg ggcccagctg     1260
gctccacggt tccagaatgt tcaggtggtc agtgttctac tcagaaatgt ctcacagccc     1320
agctgggttg caattccaga atgctggag ttttacagtg ccattccaag tcccagatgt     1380
ccctcttccc ccaaacttga ccttgaccat gtcactttac gtttgaattt ctgagctaaa    1440
gagtcagaga gattagtcac atagttgcct aaataggaga gagaaagatt atatatgcac    1500
atatacaaag acagtgtcta tttatgattg atttatttat ttataaattt acttatgggt    1560 ggtaagggc aaaaaagagg cccacacctt gatatccagg ccataccagg gtatcccttg     1620
tcccttcacc cccatttctg acctcagttc ctgaggggg gaaagggtga aagagaaacc     1680 acgtatttg ttattatttt ggattatttt ttatcgaaga gatcatagaa accagagcct     1740
```

```
tctccccagg cctgccctcc tcgggtttgg aaggggaaca caccagcctc tggttttta      1800 ttttttaag  aagccatcac ctgagcaacc aaaaattcct ctgcgctggg gtccgactgc      1860
cctctggtgg ccatttgggg aaaactgcag cccggccagg cagctgggac cagaatgcaa      1920
ccccagctcc actccagcct ggcgtccagg ccacagcca  tggcctgggg gccaagcctc      1980
accctgcggt gccctaaagg agggggggca cgagccaaca ccccaccct  ctgccaaccg      2040 gggtatggcc cccagtgcat tccctgttcc cgtctccaac ccaactcaat aaaaaatgat      2100
tttgtcataa aaaaaaaaaa aaaaaaaaaa aaaaaaaaaa aaaaa                     2145
```

<210> SEQ ID NO 5
<211> LENGTH: 330
<212> TYPE: PRT
<213> ORGANISM: Homo sapiens

<400> SEQUENCE: 5

```
Met Met Trp Gly Ala Gly Ser Pro Leu Ala Trp Leu Ser Ala Gly Ser
1               5                   10                  15

Gly Asn Val Asn Val Ser Ser Val Gly Pro Ala Glu Gly Pro Thr Gly
                20                  25                  30

Pro Ala Ala Pro Leu Pro Ser Pro Lys Ala Trp Asp Val Leu Cys
        35                  40                  45

Ile Ser Gly Thr Leu Val Ser Cys Glu Asn Ala Leu Val Val Ala Ile
    50                  55                  60

Ile Val Gly Thr Pro Ala Phe Arg Ala Pro Met Phe Leu Leu Val Gly
65                  70                  75                  80

Ser Leu Ala Val Ala Asp Leu Leu Ala Gly Leu Gly Leu Val Leu His
                85                  90                  95

Phe Ala Ala Val Phe Cys Ile Gly Ser Ala Glu Met Ser Leu Val Leu
            100                 105                 110

Val Gly Val Leu Ala Met Ala Phe Thr Ala Ser Ile Gly Ser Leu Leu
        115                 120                 125

Ala Ile Thr Val Asp Arg Tyr Leu Ser Leu Tyr Asn Ala Leu Thr Tyr
    130                 135                 140

Tyr Ser Glu Thr Thr Val Thr Arg Thr Tyr Val Met Leu Ala Leu Val
145                 150                 155                 160

Trp Gly Gly Ala Leu Gly Leu Gly Leu Leu Pro Val Leu Ala Trp Asn
                165                 170                 175

Cys Leu Asp Gly Leu Thr Thr Cys Gly Val Val Tyr Pro Leu Ser Lys
            180                 185                 190

Asn His Leu Val Val Leu Ala Ile Ala Phe Phe Met Val Phe Gly Ile
        195                 200                 205

Met Leu Gln Leu Tyr Ala Gln Ile Cys Arg Ile Val Cys Arg His Ala
    210                 215                 220

Gln Gln Ile Ala Leu Gln Arg His Leu Leu Pro Ala Ser His Tyr Val
225                 230                 235                 240

Ala Thr Arg Lys Gly Ile Ala Thr Leu Ala Val Val Leu Gly Ala Phe
                245                 250                 255

Ala Ala Cys Trp Leu Pro Phe Thr Val Tyr Cys Leu Leu Gly Asp Ala
            260                 265                 270

His Ser Pro Pro Leu Tyr Thr Tyr Leu Thr Leu Leu Pro Ala Thr Tyr
        275                 280                 285

Asn Ser Met Ile Asn Pro Ile Ile Tyr Ala Phe Arg Asn Gln Asp Val
    290                 295                 300

Gln Lys Val Leu Trp Ala Val Cys Cys Cys Cys Ser Ser Ser Lys Ile
```

```
                305                 310                 315                 320

Pro Phe Arg Ser Arg Ser Pro Ser Asp Val
                325                 330

<210> SEQ ID NO 6
<211> LENGTH: 2180
<212> TYPE: DNA
<213> ORGANISM: Homo sapiens

<400> SEQUENCE: 6
accccgcgcg gttccacgcc cctggccgcg gcccgggcgc tgcgctgctc gacgcggcgg    60
gcggcgggcg gggaccgggg gcggggggcgg cggcggcggc cgggagagcg gaggaggcgg   120
agcagggagc cggagcggg ctggcccgcg ctcctcctgc tggctgggga ttttccagcc    180
tgggcgctga cgccgcggac ctccctgcga ccgtcgcgga ccatgggcga caaagggacc    240
cgagtgttca agaaggccag tccaaatgga aagctcaccg tctacctggg aaagcgggac    300 tttgtgacc acatcgacct cgtggaccct gtggatggtg tggtcctggt ggatcctgag    360
tatctcaaag agcggagagt ctatgtgacg ctgacctgcg ccttccgcta tggccgggag    420
gacctggatg tcctgggcct gacctttcgc aaggacctgt tgtgggccaa cgtacagtcg    480
ttcccaccgg cccccgagga caagaagccc ctgacgcggc tgcaggaacg cctcatcaag    540
aagctgggcg agcacgctta ccctttcacc tttgagatcc ctccaaacct tccatgttct    600
gtgacactgc agccggggcc cgaagacacg gggaaggctt gcggtgtgga ctatgaagtc    660
aaagccttct cgcgcgagaa tttggaggag aagatccaca gcggaattc tgtgcgtctg    720 gtcatccgga aggttcagta tgccccagag aggcctggcc cccagcccac agccgagacc    780
accaggcagt tcctcatgtc ggacaagccc ttgcacctag aagcctctct ggataaggag    840
atctattacc atggagaacc catcagcgtc aacgtccacg tcaccaacaa caccaacaag    900
acggtgaaga agatcaagat ctcagtgcgc cagtatgcag acatctgcct tttcaacaca    960
gctcagtaca agtgccctgt tgccatggaa gaggctgatg acactgtggc acccagctcg   1020
acgttctgca aggtctacac actgaccccc ttcctagcca ataaccgaga gaagcggggc   1080
ctcgccttgg acgggaagct caagcacgaa gacacgaact tggcctctag caccctgttg   1140
agggaaggtg ccaaccgtga gatcctgggg atcattgttt cctacaaagt gaaagtgaag   1200
ctggtggtgt ctcggggcgg cgacgtggcc gtggaactgc ccttcacccct aatgcacccc   1260 aagcccaaag aggaaccccc gcatcggaa gttccagaga acgagacgcc agtagatacc   1320
aatctcatag aacttgacac aaatgatgac gacattgtat ttgaggactt tgctcgccag   1380
agactgaaag gcatgaagga tgacaaggag gaagaggagg atggtaccgg ctctccacag   1440
ctcaacaaca gatagacggg ccggccctgc ctccacgtgg ctccggctcc actctcgtgc   1500
actcggatgc ttactcgtct tcttcctgtt ctggtttctt ttcccctttg ttcttccagt   1560
ttctaccagg gggcccgtg ggcttccaga tcacggtgat gaacctctgg cctcaggatt   1620
ggccccacat caccacgcca acaggaccac agcgcactgg ctccaccccca tctctgccat   1680 ctccactccc ctccttttca tgctgtctcc cagaaaagct gccagggctc tggccttgga   1740
attggacttg agatggggag cagacagggg aggatgggga atgtgggaca cggtgtggtg   1800
ggcatgaggg cttggagggg tggggatgag ggctcaagac acgagagaag atgtccacgg   1860
tcccaggtgg ttaacaaagt tctggcagct aaaagatgac cgcgttgaag gccacctcct   1920
tctggctggg aggggcagaa ctgtggacag attctcaatg cctttttgaa gttctgaccc   1980
accaaagacc ttctgccttc accctcctcc ccacctgatg tccctctgtg tctgatagtg   2040
```

```
atgttggtga agttcgtag  accccaggag tagagaaaag caactggact gactttctta   2100
ccagcagtta cctagactga ggcaagctgt gtggactcac ccaagtatat ttcagtactg   2160
tcaggctgtg acatcttagc                                              2180
```

<210> SEQ ID NO 7
<211> LENGTH: 410
<212> TYPE: PRT
<213> ORGANISM: Homo sapiens

<400> SEQUENCE: 7

```
Met Gly Asp Lys Gly Thr Arg Val Phe Lys Lys Ala Ser Pro Asn Gly
1               5                   10                  15

Lys Leu Thr Val Tyr Leu Gly Lys Arg Asp Phe Val Asp His Ile Asp
            20                  25                  30

Leu Val Asp Pro Val Asp Gly Val Val Leu Val Asp Pro Glu Tyr Leu
        35                  40                  45

Lys Glu Arg Arg Val Tyr Val Thr Leu Thr Cys Ala Phe Arg Tyr Gly
    50                  55                  60

Arg Glu Asp Leu Asp Val Leu Gly Leu Thr Phe Arg Lys Asp Leu Phe
65                  70                  75                  80

Val Ala Asn Val Gln Ser Phe Pro Pro Ala Pro Glu Asp Lys Lys Pro
                85                  90                  95

Leu Thr Arg Leu Gln Glu Arg Leu Ile Lys Lys Leu Gly Glu His Ala
            100                 105                 110

Tyr Pro Phe Thr Phe Glu Ile Pro Pro Asn Leu Pro Cys Ser Val Thr
        115                 120                 125

Leu Gln Pro Gly Pro Glu Asp Thr Gly Lys Ala Cys Gly Val Asp Tyr
    130                 135                 140

Glu Val Lys Ala Phe Cys Ala Glu Asn Leu Glu Glu Lys Ile His Lys
145                 150                 155                 160

Arg Asn Ser Val Arg Leu Val Ile Arg Lys Val Gln Tyr Ala Pro Glu
                165                 170                 175

Arg Pro Gly Pro Gln Pro Thr Ala Glu Thr Thr Arg Gln Phe Leu Met
            180                 185                 190

Ser Asp Lys Pro Leu His Leu Glu Ala Ser Leu Asp Lys Glu Ile Tyr
        195                 200                 205

Tyr His Gly Glu Pro Ile Ser Val Asn Val His Val Thr Asn Asn Thr
    210                 215                 220

Asn Lys Thr Val Lys Lys Ile Lys Ile Ser Val Arg Gln Tyr Ala Asp
225                 230                 235                 240

Ile Cys Leu Phe Asn Thr Ala Gln Tyr Lys Cys Pro Val Ala Met Glu
                245                 250                 255

Glu Ala Asp Asp Thr Val Ala Pro Ser Ser Thr Phe Cys Lys Val Tyr
            260                 265                 270

Thr Leu Thr Pro Phe Leu Ala Asn Asn Arg Glu Lys Arg Gly Leu Ala
        275                 280                 285

Leu Asp Gly Lys Leu Lys His Glu Asp Thr Asn Leu Ala Ser Ser Thr
    290                 295                 300

Leu Leu Arg Glu Gly Ala Asn Arg Glu Ile Leu Gly Ile Ile Val Ser
305                 310                 315                 320

Tyr Lys Val Lys Val Lys Leu Val Val Ser Arg Gly Gly Asp Val Ala
                325                 330                 335

Val Glu Leu Pro Phe Thr Leu Met His Pro Lys Pro Lys Glu Glu Pro
            340                 345                 350
```

```
Pro His Arg Glu Val Pro Glu Asn Glu Thr Pro Val Asp Thr Asn Leu
        355                 360                 365

Ile Glu Leu Asp Thr Asn Asp Asp Ile Val Phe Glu Asp Phe Ala
370                 375                 380

Arg Gln Arg Leu Lys Gly Met Lys Asp Asp Lys Glu Glu Glu Asp
385                 390                 395                 400

Gly Thr Gly Ser Pro Gln Leu Asn Asn Arg
                405                 410

<210> SEQ ID NO 8
<211> LENGTH: 1936
<212> TYPE: DNA
<213> ORGANISM: Homo sapiens

<400> SEQUENCE: 8
ccccgcgtgt ctgctaggag agggcgggca gcgccgcggc gcgcgcgatc cggctgacgc    60
atctggcccc ggttcccaa gaccagagcg gggccgggag ggaggggaa gaggcgagag    120
cgcggagggc gcgcgtgcgc attggcgcgg ggaggagcag ggatcttggc agcgggcgag    180
gaggctgcga gcgagccgcg aaccgagcgg gcggcgggcg cgcgcaccat ggggagaaa    240
cccgggacca gggtcttcaa gaagtcgagc cctaactgca agctcaccgt gtacttgggc    300
aagcgggact tcgtagatca cctggacaaa gtggaccctg tagatggcgt ggtgcttgtg    360
gaccctgact acctgaagga ccgcaaagtg tttgtgaccc tcacctgcgc cttccgctat    420
ggccgtgaag acctggatgt gctgggcttg tccttccgca agacctgtt catcgccacc    480
taccaggcct ccccccggt gcccaaccca ccccggcccc ccacccgcct gcaggaccgg    540
ctgctgagga agctgggcca gcatgccac cccttcttct tcaccatacc ccagaatctt    600
ccatgctccg tcacactgca gccaggccca gaggatacag gaaaggcctg cggcgtagac    660
tttgagattc gagccttctg tgctaaatca ctagaagaga aaagccacaa aaggaactct    720
gtgcggctgg tgatccgaaa ggtgcagttc gccccggaga acccggcccc cagccttca    780
gccgaaacca cacgccactt cctcatgtct gaccggtccc tgcacctcga ggcttccctg    840
gacaaggagc tgtactacca tggggagccc ctcaatgtaa atgtccacgt caccaacaac    900
tccaccaaga ccgtcaagaa gatcaaagtc tctgtgagac agtacgccga catctgcctc    960
ttcagcaccg cccagtacaa gtgtcctgtg gctcaactcg aacaagatga ccaggtatct    1020
cccagctcca cattctgtaa ggtgtacacc ataaccccac tgctcagcga caaccgggag    1080
aagcggggtc tcgccctgga tgggaaactc aagcacgagg acaccaacct ggcttccagc    1140
accatcgtga aggagggtgc caacaaggag gtgctgggaa tcctggtgtc ctacagggtc    1200
aaggtgaagc tggtggtgtc tcgaggcggg gatgtctctg tggagctgcc ttttgttctt    1260
atgcacccca gccccacga ccacatcccc ctccccagac cccagtcagc cgctccggag    1320
acagatgtcc ctgtggacac caacctcatt gaatttgata ccaactatgc cacagatgat    1380
gacattgtgt ttgaggactt tgcccggctt cggctgaagg ggatgaagga tgacgactat    1440
gatgatcaac tctgctagga agcggggtgg gaagaaggga ggggatgggg ttgggagagg    1500
tgagggcagg attaagatcc ccactgtcaa tgggggattg tcccagcccc tcttcccttc    1560
ccctcacctg gaagcttctt caaccaatcc cttcacactc tctcccccat cccccccaaga    1620
tacacactgg accctctctt gctgaatgtg ggcattaatt ttttgactgc agctctgctt    1680
ctccagcccc gccgtgggtg gcaagctgtg ttcataccta aattttctgg aagggggcag    1740
tgaaaagagg agtgacagga gggaaagggg gagacaaaac tcctactctc aacctcacac    1800
```

```
caacacctcc cattatcact ctctctgccc ccattccttc aagaggagac cctttgggga    1860
caaggccgtt tctttgtttc tgagcataaa gaagaaaata aatcttttac taagcatgaa    1920
aaaaaaaaaa aaaaa                                                     1936
```

<210> SEQ ID NO 9
<211> LENGTH: 409
<212> TYPE: PRT
<213> ORGANISM: Homo sapiens

<400> SEQUENCE: 9

```
Met Gly Glu Lys Pro Gly Thr Arg Val Phe Lys Ser Ser Pro Asn
1               5                   10                  15

Cys Lys Leu Thr Val Tyr Leu Gly Lys Arg Asp Phe Val Asp His Leu
            20                  25                  30

Asp Lys Val Asp Pro Val Asp Gly Val Val Leu Val Asp Pro Asp Tyr
                35                  40                  45

Leu Lys Asp Arg Lys Val Phe Val Thr Leu Thr Cys Ala Phe Arg Tyr
    50                  55                  60

Gly Arg Glu Asp Leu Asp Val Leu Gly Leu Ser Phe Arg Lys Asp Leu
65                  70                  75                  80

Phe Ile Ala Thr Tyr Gln Ala Phe Pro Pro Val Pro Asn Pro Pro Arg
                85                  90                  95

Pro Pro Thr Arg Leu Gln Asp Arg Leu Leu Arg Lys Leu Gly Gln His
                100                 105                 110

Ala His Pro Phe Phe Phe Thr Ile Pro Gln Asn Leu Pro Cys Ser Val
                115                 120                 125

Thr Leu Gln Pro Gly Pro Glu Asp Thr Gly Lys Ala Cys Gly Val Asp
130                 135                 140

Phe Glu Ile Arg Ala Phe Cys Ala Lys Ser Leu Glu Glu Lys Ser His
145                 150                 155                 160

Lys Arg Asn Ser Val Arg Leu Val Ile Arg Lys Val Gln Phe Ala Pro
                165                 170                 175

Glu Lys Pro Gly Pro Gln Pro Ser Ala Glu Thr Thr Arg His Phe Leu
                180                 185                 190

Met Ser Asp Arg Ser Leu His Leu Glu Ala Ser Leu Asp Lys Glu Leu
                195                 200                 205

Tyr Tyr His Gly Glu Pro Leu Asn Val Asn Val His Val Thr Asn Asn
                210                 215                 220

Ser Thr Lys Thr Val Lys Lys Ile Lys Val Ser Val Arg Gln Tyr Ala
225                 230                 235                 240

Asp Ile Cys Leu Phe Ser Thr Ala Gln Tyr Lys Cys Pro Val Ala Gln
                245                 250                 255

Leu Glu Gln Asp Asp Gln Val Ser Pro Ser Ser Thr Phe Cys Lys Val
                260                 265                 270

Tyr Thr Ile Thr Pro Leu Leu Ser Asp Asn Arg Glu Lys Arg Gly Leu
                275                 280                 285

Ala Leu Asp Gly Lys Leu Lys His Glu Asp Thr Asn Leu Ala Ser Ser
                290                 295                 300

Thr Ile Val Lys Glu Gly Ala Asn Lys Glu Val Leu Gly Ile Leu Val
305                 310                 315                 320

Ser Tyr Arg Val Lys Val Lys Leu Val Val Ser Arg Gly Gly Asp Val
                325                 330                 335

Ser Val Glu Leu Pro Phe Val Leu Met His Pro Lys Pro His Asp His
                340                 345                 350
```

```
-continued

Ile Pro Leu Pro Arg Pro Gln Ser Ala Ala Pro Glu Thr Asp Val Pro
        355                 360                 365

Val Asp Thr Asn Leu Ile Glu Phe Asp Thr Asn Tyr Ala Thr Asp Asp
    370                 375                 380

Asp Ile Val Phe Glu Asp Phe Ala Arg Leu Arg Leu Lys Gly Met Lys
385                 390                 395                 400

Asp Asp Asp Tyr Asp Asp Gln Leu Cys
                405

<210> SEQ ID NO 10
<211> LENGTH: 21
<212> TYPE: RNA
<213> ORGANISM: Artificial Sequence
<220> FEATURE:
<223> OTHER INFORMATION: Non-silencing siRNA

<400> SEQUENCE: 10
aauucuccga acgugucacg u                                          21
```